(12) United States Patent
Bailey et al.

(10) Patent No.: US 8,562,826 B2
(45) Date of Patent: Oct. 22, 2013

(54) SUPPORTING STRUCTURES FOR PREPARATIVE CHROMATOGRAPHY COLUMNS

(75) Inventors: Daniel M. Bailey, Hampton, NH (US); Philippe Vernot, Saint Privat (FR); Sebastien Lefebvre, Saint Saturnin (FR)

(73) Assignee: Bio-Rad Laboratories, Inc., Hercules, CA (US)

( * ) Notice: Subject to any disclaimer, the term of this patent is extended or adjusted under 35 U.S.C. 154(b) by 925 days.

(21) Appl. No.: 12/704,336

(22) Filed: Feb. 11, 2010

(65) Prior Publication Data
US 2010/0133165 A1 Jun. 3, 2010

Related U.S. Application Data

(62) Division of application No. 11/955,497, filed on Dec. 13, 2007, now Pat. No. 7,686,953.

(60) Provisional application No. 60/869,819, filed on Dec. 13, 2006.

(51) Int. Cl.
*B01D 15/08* (2006.01)

(52) U.S. Cl.
USPC ......... 210/198.2; 210/656; 210/232; 210/241

(58) Field of Classification Search
USPC .............. 210/635, 656, 659, 198.2, 232, 241; 95/82; 96/101; 422/70
See application file for complete search history.

(56) References Cited

U.S. PATENT DOCUMENTS

| | | | | |
|---|---|---|---|---|
| 6,001,260 A | * | 12/1999 | Hatch et al. | 210/656 |
| 6,736,974 B1 | * | 5/2004 | Mann | 210/656 |
| 2006/0196832 A1 | * | 9/2006 | Perreault et al. | 210/656 |

FOREIGN PATENT DOCUMENTS

| | | |
|---|---|---|
| WO | WO 2005/056156 A1 | 6/2005 |
| WO | WO 2006/048058 A1 | 5/2006 |

* cited by examiner

*Primary Examiner* — Ernest G Therkorn
(74) *Attorney, Agent, or Firm* — Kilpatrick Townsend & Stockton LLP

(57) ABSTRACT

The plunger used as the upper enclosure in a preparative chromatography column is suspended by one or more rods that are supported by a frame through coupling connections on the frame that can fix the position of the rod(s) relative to the frame, while the position of the rod(s) is controlled by a motorized drive system that is suspended above the column. The drive system is mounted either to the column lid or to a functional plate positioned a short distance above the column lid. These constructions allow the plunger to be raised and lowered so that the column and its parts can be exchanged, all without the need for a hoist or crane.

7 Claims, 9 Drawing Sheets

SUPPORTING STRUCTURES FOR PREPARATIVE CHROMATOGRAPHY COLUMNS

CROSS-REFERENCE TO RELATED APPLICATION

This application is a division of U.S. patent application Ser. No. 11/955,497, filed Dec. 13, 2007, now U.S. Pat. No. 7,686,953, which claims the benefit of U.S. Provisional Patent Application No. 60/869,819, filed Dec. 13, 2006. The contents of both applications cited in this paragraph are incorporated herein by reference in their entirety.

BACKGROUND OF THE INVENTION

This invention resides in a frame for supporting and manipulating the parts of a chromatography column of variable packing height and for exchanging columns of different sizes. The chromatography columns with which the present invention is primarily contemplated for use are preparative chromatography columns designed for plug flow of a mobile phase through a packed bed of solid or semi-solid stationary phase. The width of the typical column is large enough that the bed can accommodate a commercially useful throughput rate. In some cases, the column width exceeds 1 meter. The depth of the column is limited however to maintain a pressure drop low enough to avoid a high pump pressure or a high power requirement. Columns of this nature contain a plunger or piston head that is lowered to contact and compress the solid phase to the desired height. With the mobile phase entering the bed from the top, the plunger also includes a distributor plate to spread the mobile phase across the full width of the bed, thereby making maximal use of the bed.

The maintenance of these chromatography columns requires that the plunger be periodically removed to perform such functions as replacing its parts, replacing the packed bed, and cleaning the interior of the column. In many cases as well, a column must be exchanged for one of a different height or diameter, and a plunger to match. With columns of the sizes cited above, these operations typically require a hoist or crane to lift the plunger and to clear the column from the connecting instrumentation and supply and discharge lines. These operations are labor-intensive and capital-intensive. These concerns are particularly acute when operation of the column requires a clean room or a high clearance above the column, or both.

SUMMARY OF THE INVENTION

The present invention addresses these concerns by providing a frame with coupling connections that can support the plunger through a suspending rod or series of rods, combined with a motorized drive system that moves the rod(s) vertically to cause the plunger to move up and down within the column or up and out of the column. In certain embodiments, the column rests on a column skid that can be moved into position within the frame or out of the frame, and the drive system is secured to a movable platform above the column. In other embodiments, the frame can be moved into position over the column or out of such position, and the drive system is secured to the column lid. In all embodiments, the plunger can be raised and lowered, and the columns and their component parts exchanged, without the need for a hoist or crane. Certain embodiments include a functional plate that is either specifically constructed for a particular column or can be used on columns of different diameters, for the various connections to the top of the column. These and other objects, features, and advantages of the invention will be more apparent from the accompanying figures and the description that follows.

DETAILED DESCRIPTION OF THE INVENTION AND PREFERRED EMBODIMENTS

Figure 1:
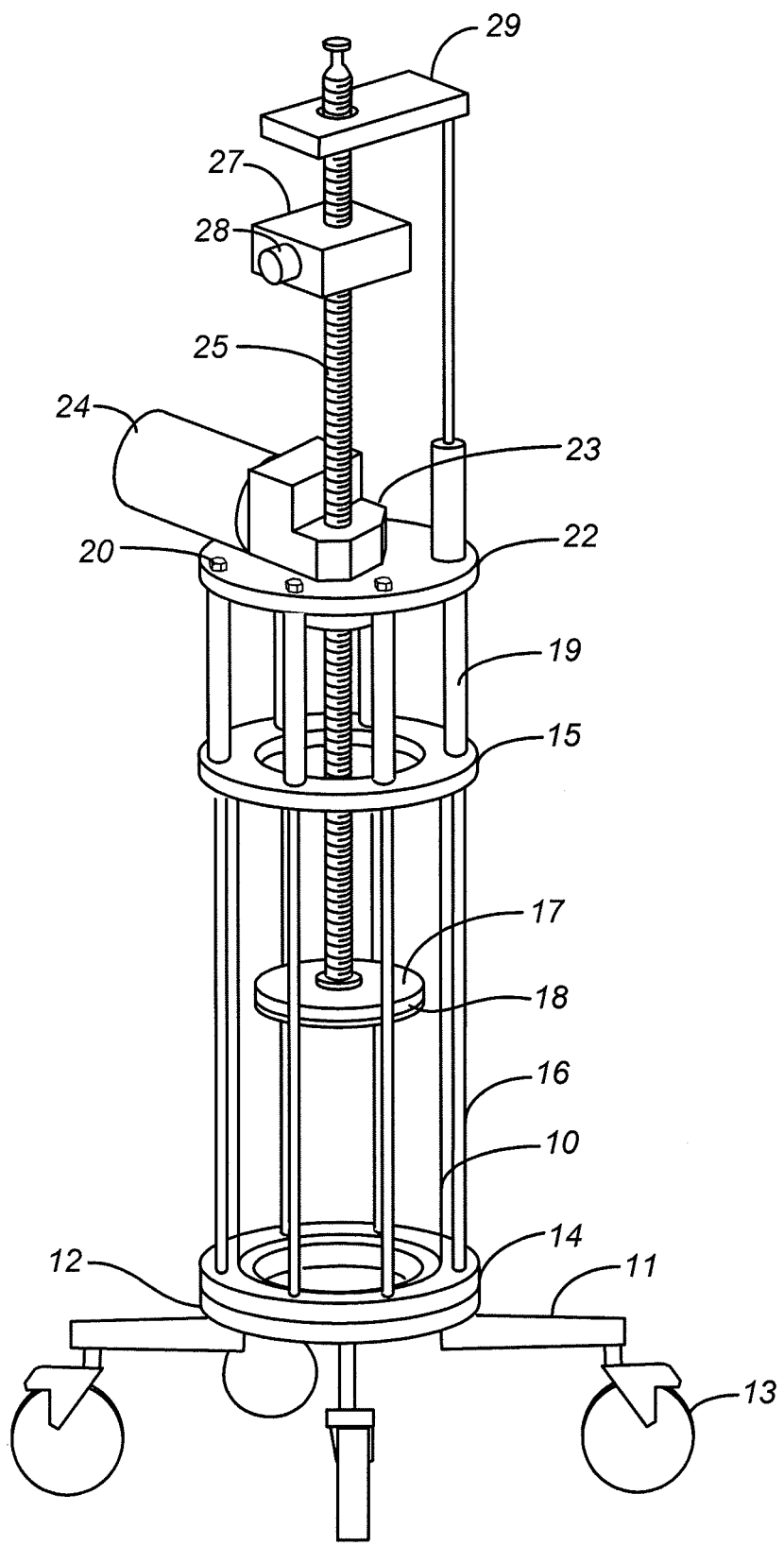
FIG. 1 is a perspective view of a preparatory chromatography column and skid, representing one example of this invention.

While the features defining this invention are capable of implementation in a variety of constructions, the invention as a whole will be best understood by a detailed examination of specific embodiments. Two such embodiments are shown in the drawings.

Figure 2:
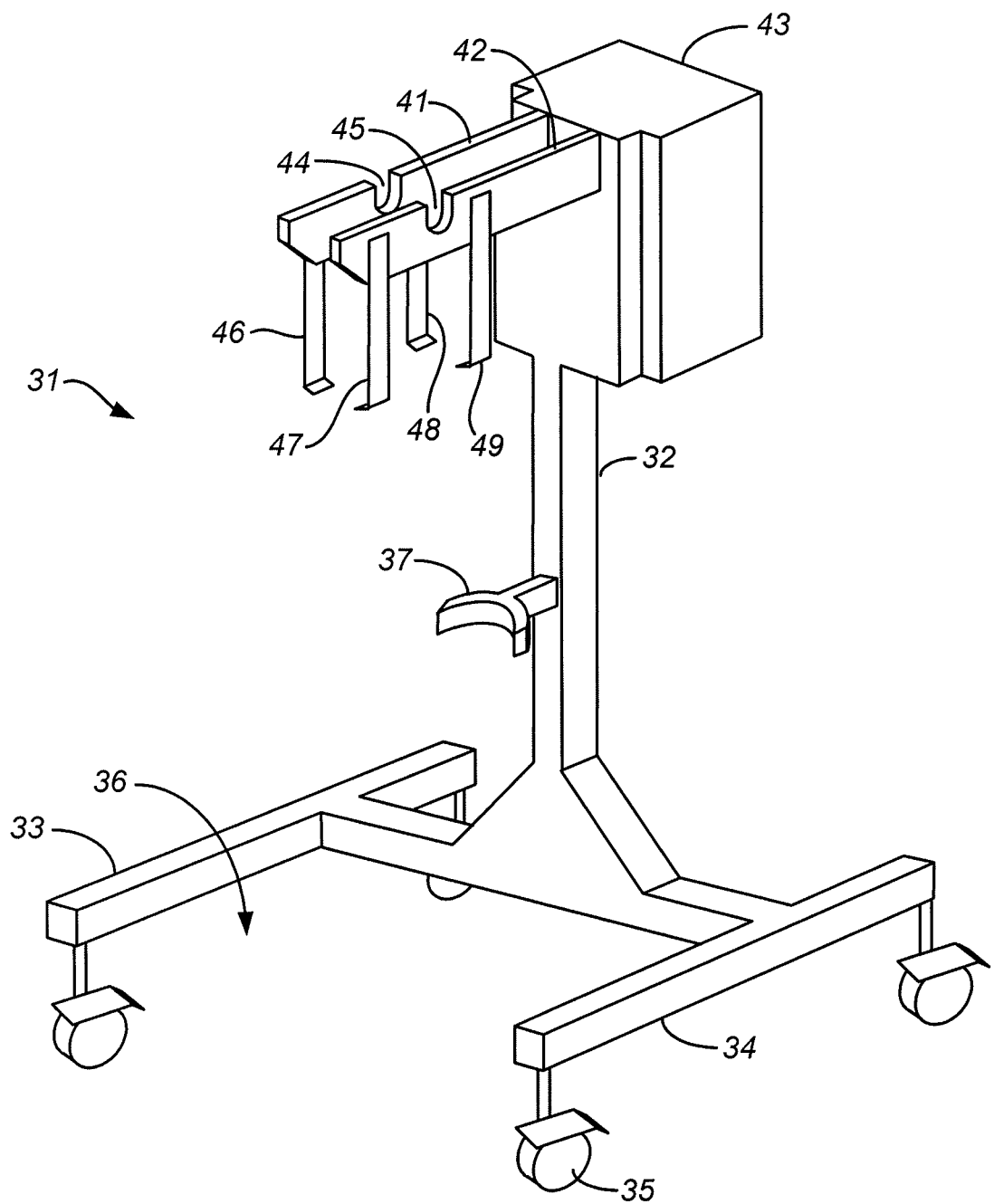
FIG. 2 is a perspective view of a frame in accordance with this invention designed for use with the column and skid of FIG. 1.
Figure 3:
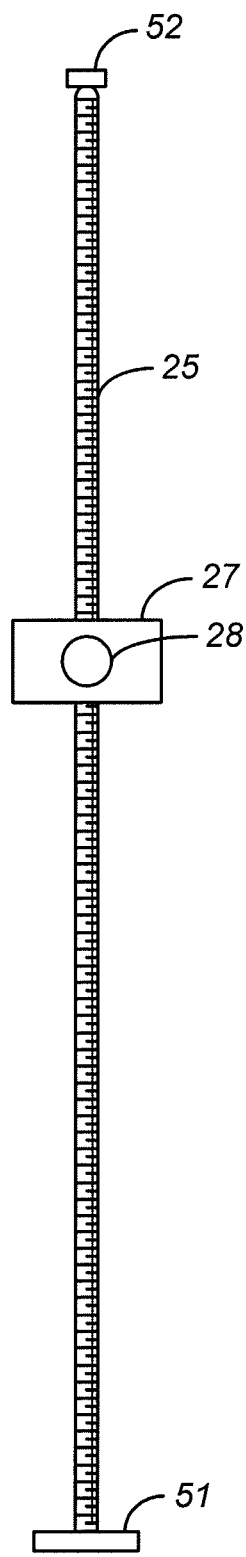
FIG. 3 is a front view of a hollow screw which is one of the components of the column and skid of FIG. 1.
Figure 4:
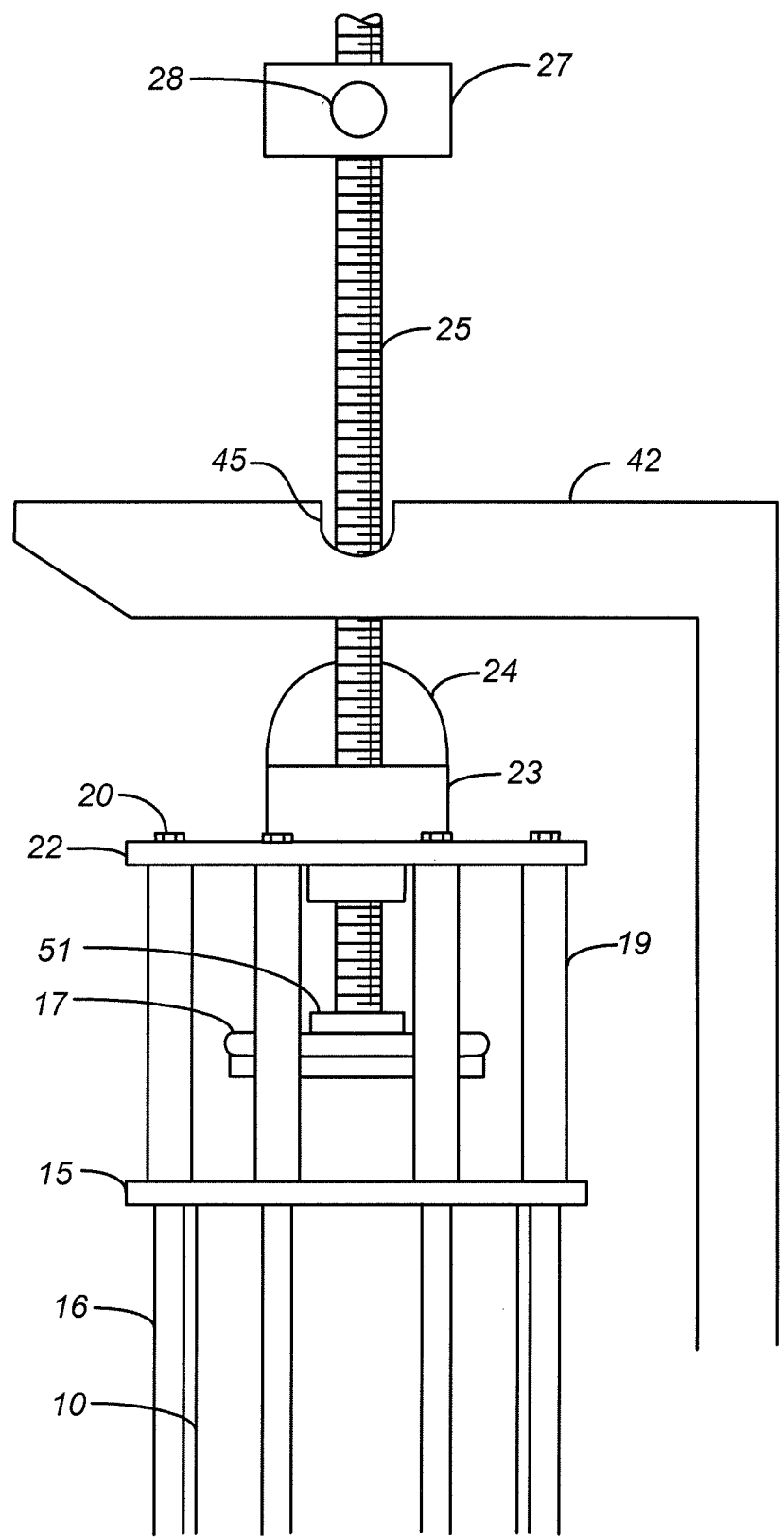
FIG. 4 is a front view of an upper portion of the column and skid of FIG. 1 and an upper portion of the frame of FIG. 4 in one position.

The first of these two embodiments is shown in FIGS. 1 through 7. FIG. 1 depicts a column in accordance with the invention and the skid on which it rests, in condition for use in a chromatographic procedure. While the column tube 10 is typically constructed of stainless steel, it is shown as transparent in FIG. 1 to render the remaining components visible and more readily understandable. The skid 11 includes a bottom plate 12 and a set of caster wheels 13, while the column mount includes a base (i.e., lower) ring 14, an upper ring 15, and a series of supporting rods 16 (six in this embodiment) joining the two rings and forming a circle around the peripheries of the rings. A column space is thus defined between the lower and upper rings 14, 15 and within the circle formed by the supporting rods 16. The column tube 10 resides within this space. The plunger 17 (also referred to as a piston head) fits inside the column tube 10 and contains a circumferential gasket 18 that seals against the inner surface of the column tube. The gasket can be inflatable to allow free movement within the column, and into and out of the column, when deflated and to seal against the column wall when inflated. Above the upper ring 15 are a series of spacer rods 19 that support a functional plate 22 (also referred to as a "top plate") a short distance above the upper ring 15. The spacer rods 19 are detachably secured to the functional plate 22 by nuts 20 that engage threaded extensions (not visible) of the spacer rods, and also detachable secured to the upper ring 15 by threaded connections (also not visible) extending upward from the upper ring. Secured to the functional plate 22 are a gear box 23 and a motor 24, whose functions are described below. A flow distribution that achieves plug flow, or a flow approximating plug flow, is achieved by distributors inside the plunger 17 and in the center of the base ring 14. The column can be used either with the spacer rods 19 in place as shown in FIG. 4 or without the spacer rods, in which case the functional plate 22 is in contact with the upper ring 22 and the plate and ring can be bolted together by removable bolts or any removable coupling elements.

The plunger 17 is mounted to the lower end of a central screw 25, which is a hollow rod threaded on its outer surface. The axis of the central screw 25 coincides with the axes of the lower and upper rings 14, 15, the lower and upper rings thus being parallel and coaxial with the central screw 25. With its hollow center, this central screw 25 serves as a process line to supply the mobile phase to the column, and the external threads of the screw, in conjunction with the gear box 23, form a worm gear for moving the screw 25, and hence the plunger 17, up and down along the axis. The upper ring 15 has a central opening 26 through which the plunger 17 can be raised when operations require that the plunger be lifted entirely out of the column. The plunger will be lifted out of the column, for example, to clear the column or the plunger for removal and replacement and for access to the column interior for purposes of cleaning and other maintenance.

A further component shown in FIG. 1 is a special nut 27. In this embodiment, knobs protrude from each of two opposing sides of the nut, one knob 28 being visible in the Figure. A still further component shown in the Figure is a screw guide 29. The nut is threaded to complement the threaded outer surface of the central screw 25 and is movable along the screw in the axial direction. The functions of the nut 27 and the knobs 28 will be apparent from the succeeding figures and description. In general, however, the knobs 28 serve to couple the nut to the frame. Various alternate structures that are equivalent to these knobs will be readily apparent to the skilled user. The screw guide 29 stabilizes the central screw 25 and helps keep it in alignment.

The frame 31 that supports the upper components of the column skid and assists in their manipulation is shown in FIG. 2. In this embodiment, the frame 31 includes an upright post 32 and two parallel base rails 33, 34 supported by caster wheels 35. The base rails 33, 34 are separated by a gap 36 to receive the column skid (FIG. 1), and extending into the gap from the post 32 is a brace 37 that will contact the column tube 10 (FIG. 1) to stabilize the position of the column and center the column in the frame. The frame can be constructed in a variety of ways, but its most important features are a pair of parallel horizontal beams 41, 42 that extend over the area that will be occupied by the column skid and that will support the entire weight of the column. A controller 43, which is mounted to the frame, includes a pneumatic supply that can be connected to the plunger gasket 18 (FIG. 1) to inflate the gasket to form a tight seal between the plunger and the column wall. The spacing between the horizontal beams 41, 42 allows the passage of the central screw 25 and loosely accommodates the nut 27 (FIG. 1), and yet is narrow enough to engage the parallel sides of the nut and thereby prevent the nut from rotating when the nut is between the beams. Each of the horizontal beams 41, 42 contains a notch 44, 45. Each notch is sized and arranged to receive one of the knobs 28 protruding from the sides of the nut. The frame also includes downwardly depending vertical supports 46, 47, 48, 49 that are removable. The function of these supports is described below.

FIG. 3 shows the central screw 25 and the nut 27 separated from the other components. At the base or bottom end of the screw is a mounting flange 51 that can be connected and disconnected from the plunger 17 (FIG. 1) by bolts (not shown) for different operations of the unit as a whole. At the top or upper end of the screw is a pipe or tube connection 52 to join the screw to a source of supply of the mobile phase which will flow through the hollow interior of the screw and into the column tube 10. As noted above, the nut 27 can be manually rotated to vary its position along the height of the screw. The nut 27 will occupy different positions at different stages of the manipulation of the column and its various connecting parts.

Figure 5:
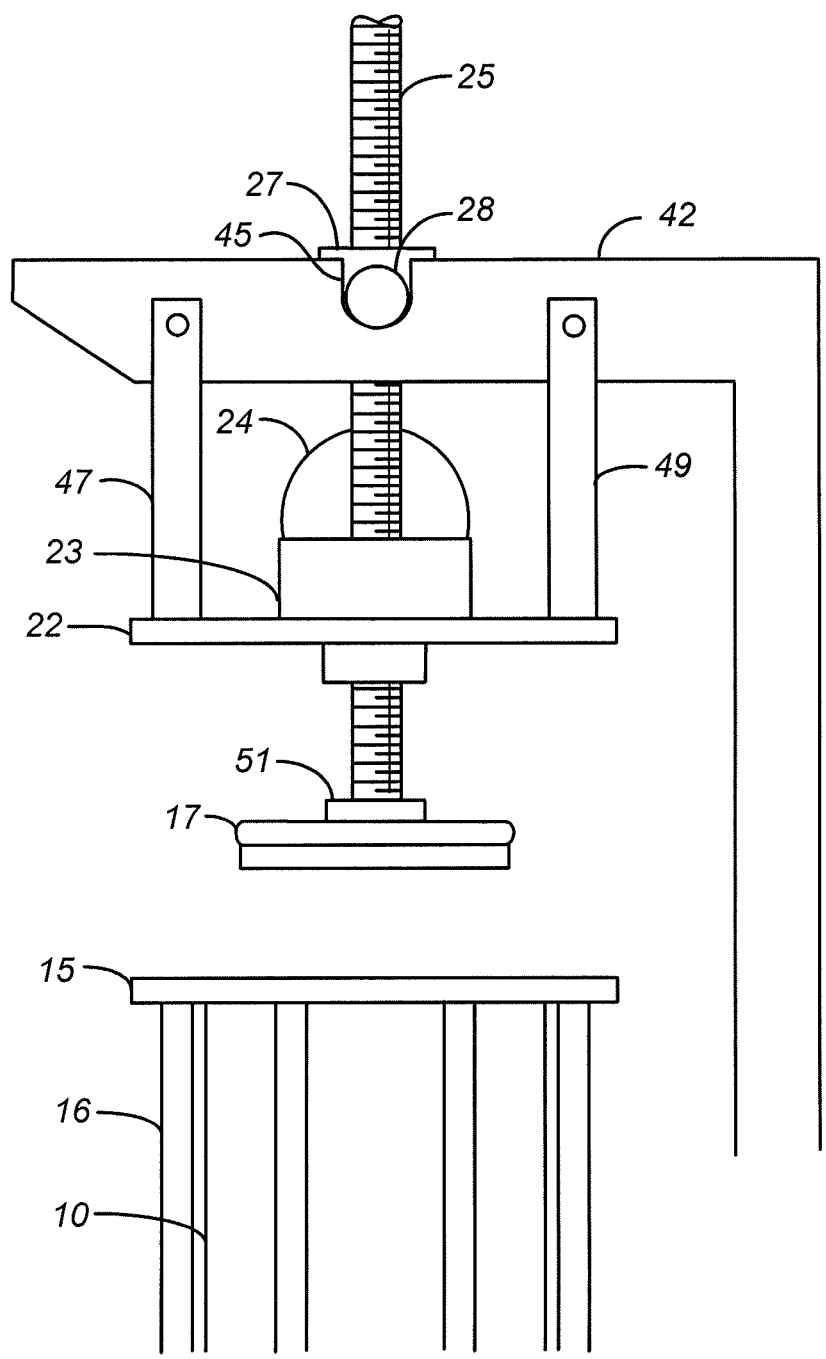
FIG. 5 is a front view of an upper portion of the column and skid of FIG. 1 and an upper portion of the frame of FIG. 4 in a second position.

Enlarged side views of two mounting configurations of the various parts of the unit are shown in FIGS. 4 and 5, respectively, including one horizontal beam 42 of the frame and various components of the column toward the upper end of the column. In both figures, the plunger 17 is raised above the column tube 10. In FIG. 4, the spacers 19 are installed to secure the upper ring 15 to the top plate 22, and the nut 27 is poised above the horizontal beams of the frame. Operation of the motor 24 and gear box 23 will raise and lower the central screw 25 and thereby cause the plunger 17 to be lowered into or raised above the column tube 10. The column tube can then be emptied and refilled, particularly those columns that are constructed to allow emptying and filling through ports in the bottom. In FIG. 5, the spacers 19 have been removed, and the downwardly depending vertical supports, of which only two 47, 49 are visible, have been installed. The top plate 22 is thereby secured to the horizontal beams 42 of the frame, and the column tube 10 and its supporting rods 16 can be removed and replaced with a different column and supporting rods. The plunger 17 can also be disconnected from the mounting flange 51 at the lower end of the central screw 25 and replaced. Also in FIG. 5, the nut 27 has been lowered between the horizontal beams far enough that the knobs 28 are engaged by the notches 45, preventing further downward movement of the central screw 25. A slotted removable stop ring (not shown) can be inserted above the mounting flange 51 to protect the nuts and other fastening components at the top of the flange 17 from contact with the base top plate 22 and gear box 23. Quick-release pins such as Cotter pins can also be included to retain the knobs in position inside the notches.

The following is one example of a procedure that can be used to separate the column tube 10 from the plunger 17. This procedure involves the use of the frame without the vertical supports 46, 47, 48, 49. As noted above, chromatographic separations can be performed in the column either with the spacer rods 19 in place as shown in FIG. 1 or without the spacer rods (in which case the functional plate 22 is bolted directly to the upper column ring 15). With or without the spacer rods 19, the separation procedure is begun by moving the column and skid into position against the frame 31 of FIG. 2, with the vertical supports 46, 47, 48, 49 having first been removed from the frame. Once the column and skid are in place, the motor 24 is energized, and since the functional plate 22 to which the motor 24 and gear box 23 are mounted is fixed to the column (either directly or through the spacer rods 19), the worm gear formed by the central screw 25 and the gear box 23 lifts the plunger 17 upward. When the spacer rods 19 are in place, the motor can pull the plunger out of the column tube 10 and into the gap formed between the upper column plate 15 and the functional plate 22 by the spacer rods as shown in FIG. 4. The screw 25 in this raised position is then coupled to the frame by lowering the nut 27 into the space between the frame beams 41, 42 while placing the knobs 28 in the notches 45, and coupling the nut to the frame by releasable retaining pins (not shown in the drawings). With the screw coupled to the frame, the spacer rods 19 can then be removed, and the column, including column tube 10, upper and lower rings 14, 15, and column skid 11, can all be rolled out from under the frame, while the plunger 17 and central screw 25 remain suspended from the frame.

In cases where the column is used with the functional plate 22 bolted directly to the upper column ring 15 without the intervening spacer rods 19, the functional plate must be disconnected from the upper column ring before the plunger can be lifted out of the column. To accomplish this, the bolts securing the plate to the ring are removed either before or after the column and skid are placed against the frame. This disconnects not only the functional plate 22 but also the motor 24, and gear box 23 from the column. The screw 25 is then coupled to the frame as described in the preceding paragraph. With the screw thus immobilized, the motor is then energized, causing the functional plate, motor, and gear box to travel together up the screw 25. This causes the functional plate 22 to separate from the upper column ring 15, leaving a gap between the plate and the ring, while the plunger 17 remains inside the column. Alternatively, the functional plate 22 can be kept bolted to the upper column ring 15 as the motor is first energized, and as the plunger 17 rises within the column tube 10, the motor is turned off as soon as the plunger 17 contacts the underside of the functional plate 22. The bolts securing the functional plate to the upper ring are then removed and the motor energized once again to lift the functional plate above the ring to form the gap. In either case, once the gap is formed, the spacer rods 19 are installed in the gap and securely fastened to both the plate and the ring. With the spacer rods thus installed, the motor is re-energized, causing the screw 25 and plunger 17 to rise while the functional plate, motor and gear box remain stationary. The motor continues to run until the plunger 17 clears the upper column ring 15. The spacer rods 19 are then removed as described above, and the column, including column tube 10, upper and lower rings 14, 15, and column skid 11, can all be rolled away from the frame, leaving the plunger 17 and central screw 25 suspended from the frame.

In all of the above procedures, the plunger 17 can be re-installed in the column by reversing the procedure.

The following procedure is used for preparing the column for storage. The purpose of this procedure is to close off the top of the column with a cover plate (a solid non-porous disk) and to place the plunger (after having been separated from the screw) on top of the cover plate. This can be done by first raising the plunger 17 out of the column as described in the procedures above, removing the column (by its skid) out from under the frame, placing the cover plate over the upper ring 15 of the column, and returning the column and skid to the frame. The nut 27 on the screw is then engaged by lowering the nut so that the knobs 28 are lowered into the notches, and the vertical supports 46, 47, 48, 49 (FIG. 5) are then secured to both the functional plate 22 and the frame (with quick-release pins or their equivalent), coupling the functional plate to the frame. The nut 27 is then raised, first by the motor to clear it from the horizontal beams and the notches, and then by turning the nut to cause it to travel up the central screw to leave enough height between the nut and the plunger so that plunger can be lowered onto the cover plate. With the cover plate directly underneath the plunger, the plunger is then lowered by way of the motor and the central screw to rest directly on the cover plate. The mounting flange 51 that secures the plunger 17 to the screw is then disconnected from the plunger 17, and the screw is raised (again by the motor) to lift the mounting flange from the plunger. The covered column and plunger can then be rolled out from under the frame for storage.

To lift the plunger from the column cover and remove the column cover so that the column can be taken from storage and reconnected for use, a procedure can be followed that is the reverse of the procedure in the preceding paragraph. With the functional plate 22 already attached to the frame by way of the vertical supports 46, 47, 48, 49, and the central screw 25 also attached to the frame through the functional plate, the column skid with the covered column and plunger can be moved back into position in the gap 36 between the two parallel base rails 33, 34 (FIG. 2) of the frame 31. The central screw 25 is then lowered so that the mounting flange 51 contacts the plunger 17, and the mounting flange is then secured to the plunger by bolts. The central screw is then raised to lift the plunger 17 above the cover plate, and the nut 27 is lowered to engage the horizontal beams 41, 42. The retaining pins are then attached to beams to secure the knobs and hence the nut in place. The vertical supports 46, 47, 48, 49 are then removed, and the cover plate is also removed. The spacer rods 19 are then installed atop the upper ring 15 of the column and the functional plate 22 is lowered to contact the rods. The spacer rods are then secured to both the ring and the functional plate, thereby affixing the functional plate to the column. The plunger 17 can then be raised higher to allow the column to be filled from above. By manipulation of the position of the nut 27 and the central screw 25, the plunger 17 can be lowered into the column to any desired height within the column. The skid containing the column and plunger, with the central screw, functional plate, motor, and all parts necessary for chromatography can then be moved out from under the frame for use.

For columns in which the functional plate 22 is attached directly to the upper column ring 15, the step of returning the spacer rods 19 to the column can be eliminated.

Figure 6:
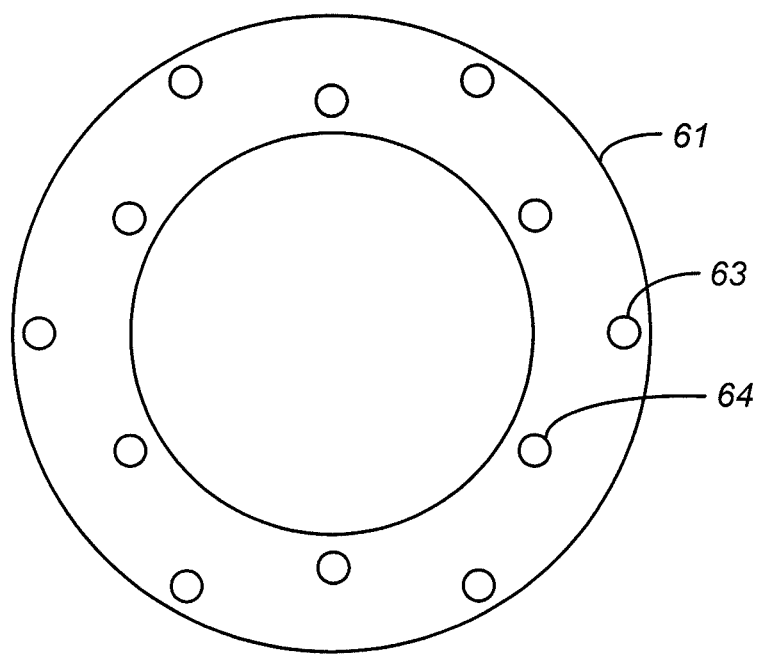
FIG. 6 is a top view of an upper plate for use in a chromatography column of this invention.
Figure 7:
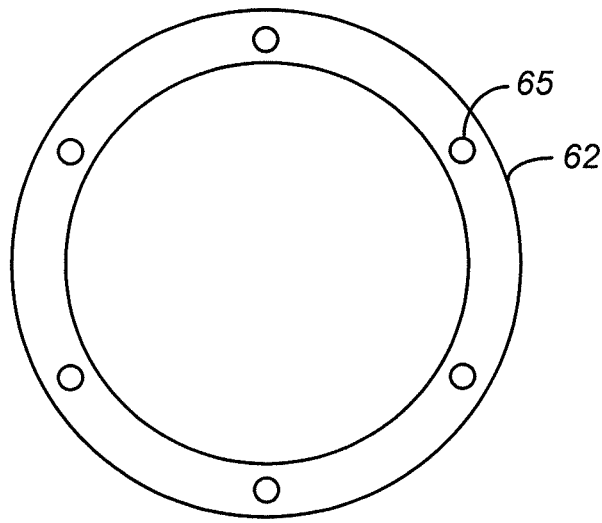
FIG. 7 is a top view of a lower plate for use with the upper plate of FIG. 6.

The structure shown in FIGS. 1 through 5 is useful for a wide range of column shapes and configurations. Included among these are the EasyPack, GelTec OCS, and InPlace (trademarks of Verdot Industrie, Riom, France) columns. A single functional plate 22 can be designed, for example, that will accommodate column tubes of different diameters. The mounts for the column tubes of different diameters will have their own upper and lower rings (corresponding to upper ring 15 of FIGS. 1, 4, and 5 and the lower ring 14 of FIG. 1) to match the columns. The upper rings can all have the same diameter, but the upper rings for smaller-diameter columns will have two sets of screw holes, i.e., an inner set and an outer set. FIG. 6 is a top view the upper ring 61 for a column of relatively small diameter, while FIG. 7 is a top view of a lower ring 62 for use with the upper ring of FIG. 6.

In the upper ring 61 of FIG. 6, the outer set of screw holes 63 (six in number in this embodiment) are aligned with the screw holes of the functional plate 22, i.e., the holes through which the spacers 19 are mounted, so that the spacers 19 will occupy the same locations for all of the different-sized columns, which are the locations shown in the preceding figures, and the same functional plate can be used with all upper rings. The inner set of screw holes 64 (six in number in this embodiment) forms a circle within the circle formed by the outer set 63. The lower ring 62 can have the same diameter as the upper ring 61 or a smaller diameter (a ring with a smaller diameter is shown), but it has a single set of screw holes 65 (six in this embodiment) that are aligned with the inner set of screw holes 64 in the upper ring 61. With the inner set of screw holes 64 in the upper ring aligned with the screw holes 65 in the lower ring, the two rings can be joined by a set of supporting rods that correspond to the column tube supporting rods 16 of FIGS. 1, 4, and 5, but that form a smaller circle to place them close to a column tube that likewise has a smaller diameter. Any number of different diameter column tubes can be accommodated by this type of construction, each having an upper ring of the same outer diameter and an outer set of screw holes at the same locations but with inner sets of screw holes at locations specific to each column tube size, together with a lower ring with screw holes aligned with the inner set of the upper ring.

The second embodiment is shown in FIGS. 8 through 13, and contains features similar to those of the first embodiment, except that the plunger is suspended by multiple threaded shafts rather than a single central screw, and the frame of fixed height is replaced by a frame of variable height to which the shafts are coupled. This embodiment does not require a threaded shaft extending above the frame, and thereby avoids the need for high clearance above the frame. This embodiment also avoids the need for removable suspending rods to couple the column to the frame. This embodiment is particularly suitable for columns that are wider and heavier than those used in the embodiment of FIGS. 1 through 7.

Figure 8:
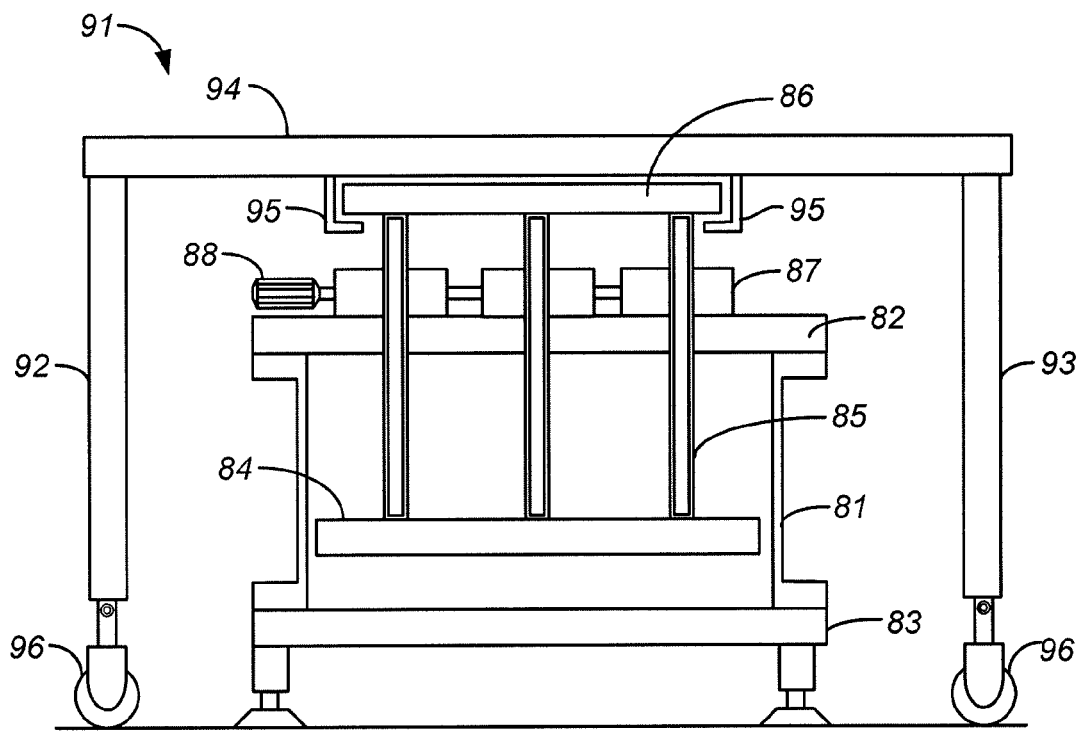
FIG. 8 is a front elevation in cross section of a second example of the present invention, including a preparative chromatography column and a movable frame.

FIG. 8 depicts the column tube 81 of this second embodiment. The column tube 81 is closed at its top with a cover plate 82 and at its bottom with a base plate 83. Passing through the cover plate 82 and into the interior of the column is a plunger 84 supported by threaded shafts 85, of which three are shown. The mobile phase enters the column through one or more of the threaded shafts 85 or through an independent set of piping, and the plunger 84, whose outer edge is inflatable to seal against the inner walls of the column tube as in the embodiment of FIGS. 1 through 7, is equipped with a distribution system to spread the flow across the width of the column and a filter to retain the solids of the slurry in the column. The base plate 83 is likewise equipped with a distribution system and filter for the same purposes as those of the plunger 84. The cover plate 82 and base plate 84 are both secured to the column tube 81 by removable bolts (not shown) or other conventional means that permit dismounting by the operator. The upper ends of the threaded shafts 85 are mounted to a coupling plate 86, so called in view of its use in coupling to the frame (as explained below), and each shaft is engaged by a separate gear box 87, with all gear boxes secured to the coupling plate 86 and driven by a common motor 88. The frame 91 has vertical legs 92, 93 of variable height supporting an upper beam 94 (or two or more beams or a platform), with downwardly extending brackets 95 mounted to the underside of the beam 94.

Figure 9:
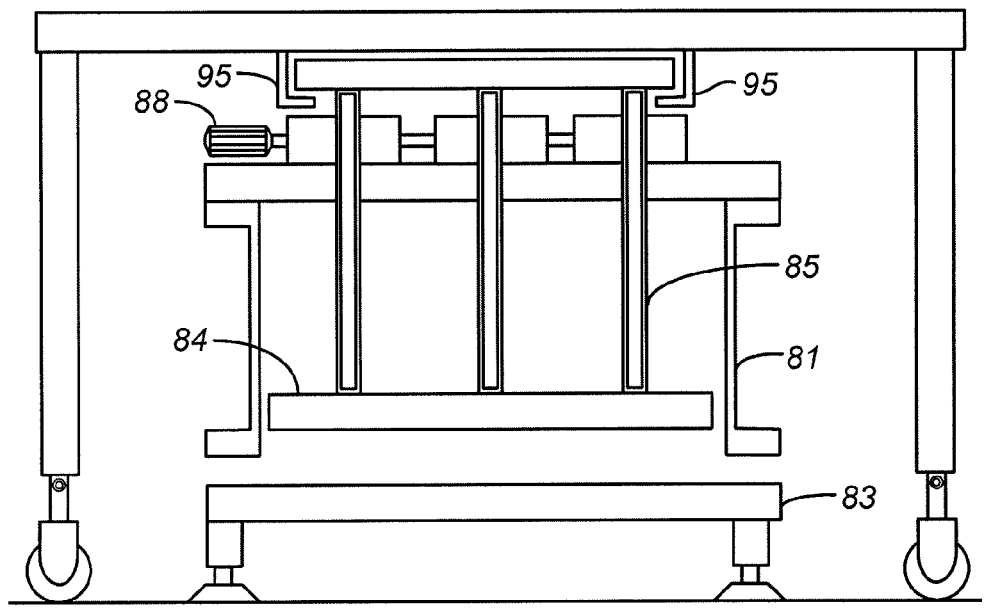
FIG. 9 depicts the column and frame of FIG. 8 in the same view, except with the column separated from and lifted above its base plate.

To gain access to the interior of the column from the bottom for purposes such as cleaning, the frame 91 is first moved into position over the column by rolling the frame on its caster wheels 96 over the column in such a manner that the brackets 95 slide over and engage the edges of the coupling plate 86, as shown in FIG. 8. Once the column is emptied of its contents through drain lines in the base plate (not shown), the operator then dismounts the column tube 81 from the base plate 83 and energizes the motor 88. This causes the gear boxes 87 to travel up the threaded shafts 85, raising the column tube 81 and cover plate 82 above the base plate 83, as shown in FIG. 9. The base plate 83 can then be removed and replaced with a pallet if desired.

Figure 10:
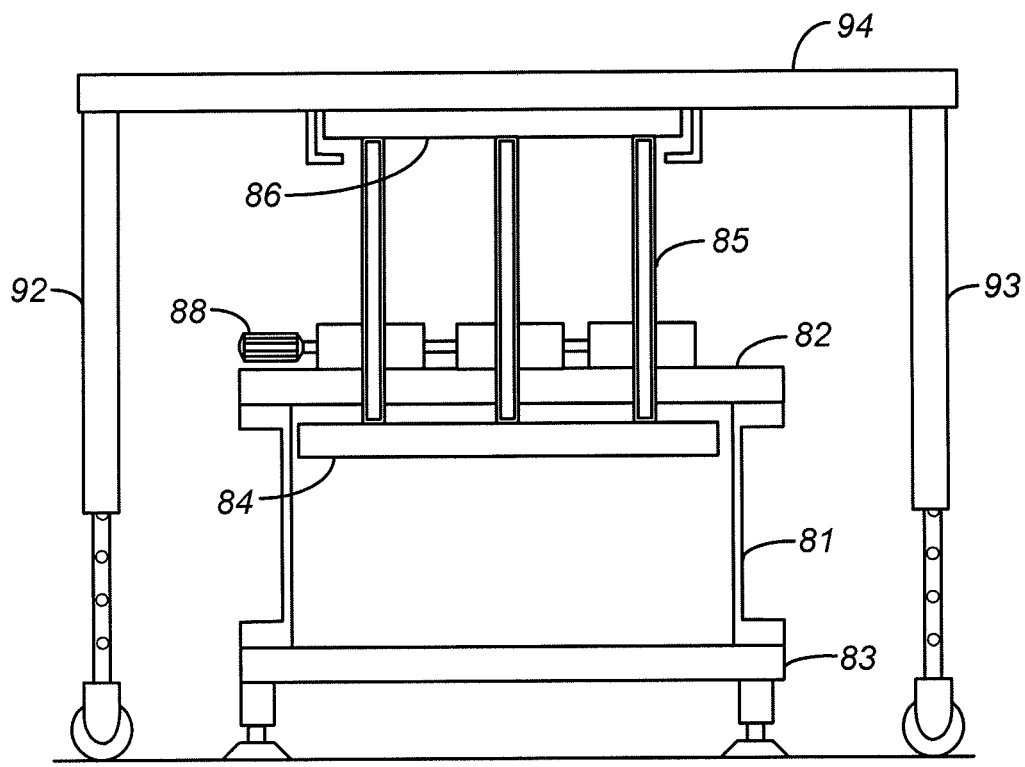
FIG. 10 shows as further stage in the manipulation of the column and frame of FIG. 8, with the frame extended vertically.
Figure 11:
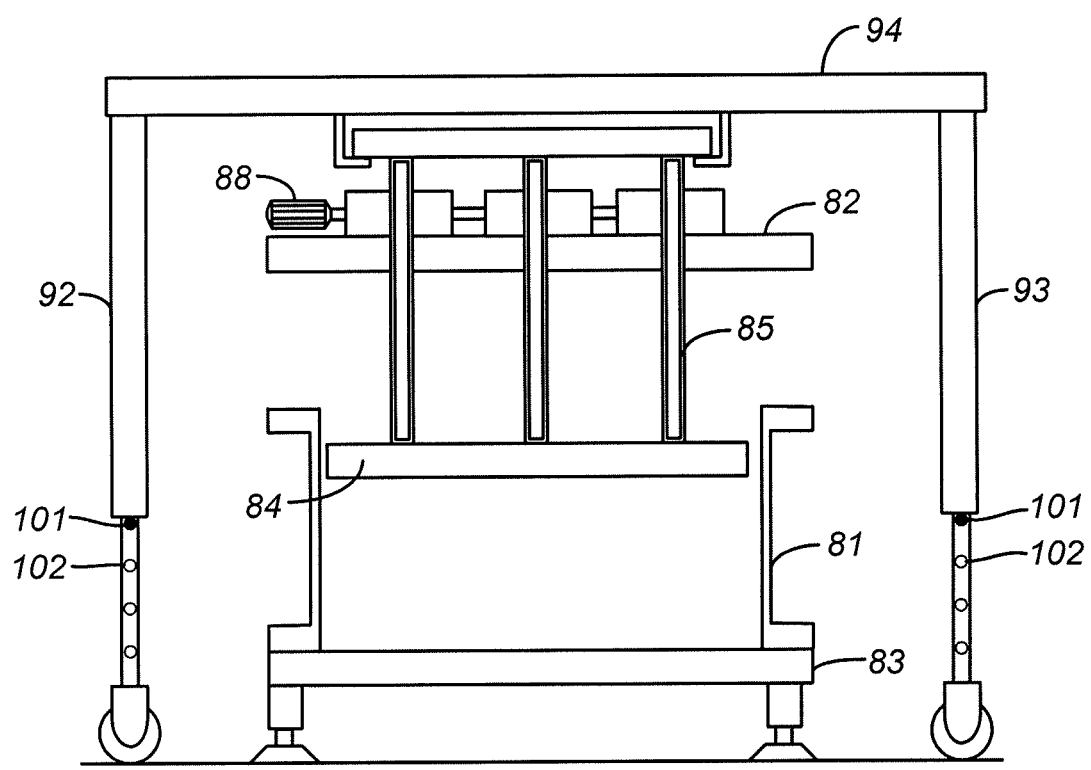
FIG. 11 is a still further stage in the manipulation of the column and frame of FIG. 8, with the column cover raised above the column.

To lift the plunger 84 and to gain access to the interior of the column from the top, the frame 91 is again moved into position as shown in FIG. 8, and the motor 88 is energized but without dismounting the column tube 81 from the base plate 83. As a result, the motor causes the threaded shafts 85 to rise, which in turn cause the plunger 84 and the coupling plate 86 to rise. The coupling plate 86 pushes the upper beam 94 of the frame upward, extending the legs 92, 93, as shown in FIG. 10. Pegs 101 are then placed in exposed holes 102 in the legs, as shown in FIG. 11, to prop up the frame in its raised position, the cover plate 82 is dismounted from the column tube 81 by the operator, and the motor 88 is once again energized to open the column by raising the cover plate 82 above the column tube 81, which is also shown in FIG. 11.

Figure 12:
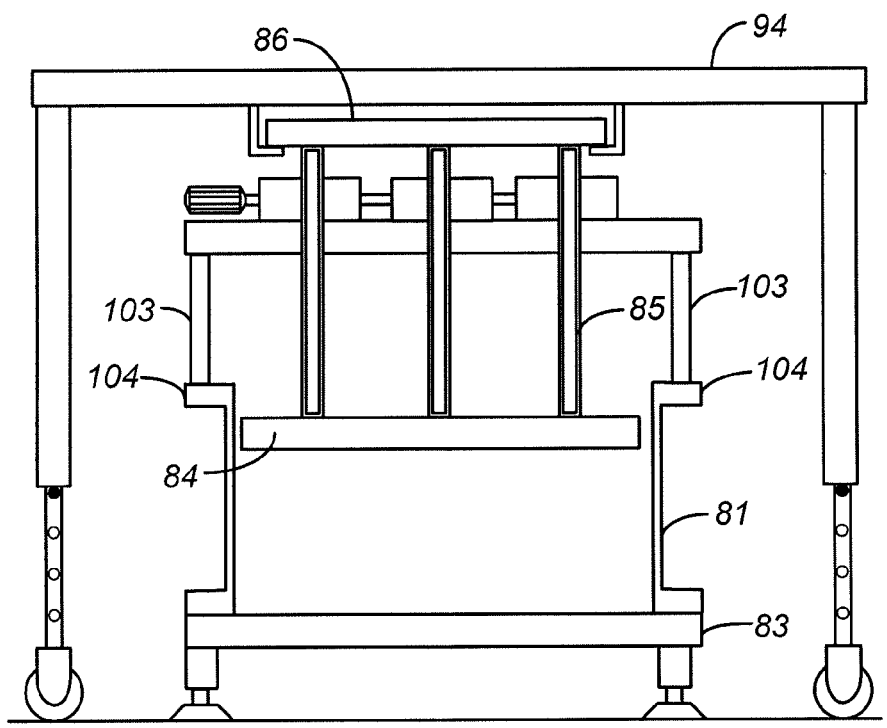
FIG. 12 shows the column and frame of FIG. 8 with spacers supporting the column cover above the column.
Figure 13:
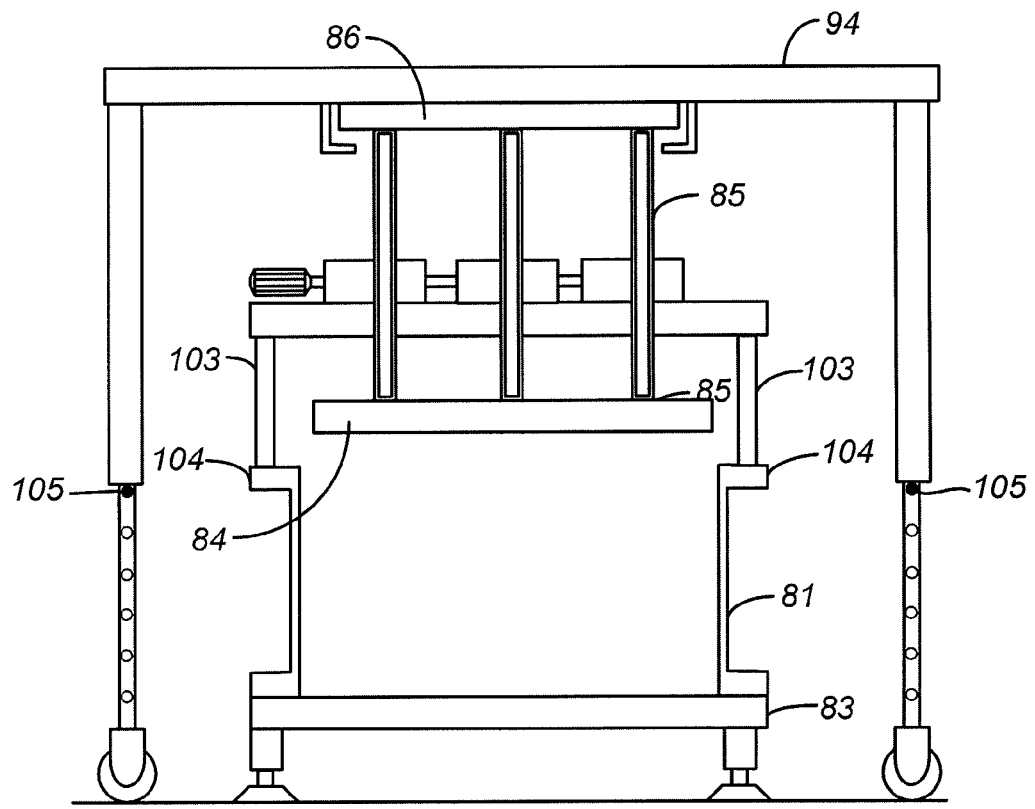
FIG. 13 shows the column and frame of FIG. 8 with the plunger raised cully out of the column.

To raise the plunger 84 higher, the frame 91 is extended further. This is accomplished by first placing spacers 103 between the cover plate 82 and the upper rim 104 of the column tube 81, as shown in FIG. 12. The motor 88 is then re-energized, causing the threaded shafts 85 to rise, pushing up the coupling plate 86 while the coupling plate pushes up the upper beam 94 of the frame. Pegs 105 are then placed in the newly exposed holes, as shown in FIG. 13, propping up the frame at its new height. The spacers 103 can then be removed, and once this is done the column tube 81 and base plate 84 can likewise be removed.

While the foregoing description describes various alternatives to the components shown in the Figures, still further alternatives will be apparent to those who are skilled in the art and are within the scope of the invention. In the claims appended hereto, the term "a" or "an" is intended to mean "one or more." The term "comprise" and variations thereof such as "comprises" and "comprising," when preceding the recitation of a step or an element, are intended to mean that the addition of further steps or elements is optional and not excluded. All patents, patent applications, and other published reference materials cited in this specification are hereby incorporated herein by reference in their entirety. Any discrepancy between any reference material cited herein and an explicit teaching of this specification is intended to be resolved in favor of the teaching in this specification. This includes any discrepancy between an art-understood definition of a word or phrase and a definition explicitly provided in this specification of the same word or phrase.

What is claimed is:

1. A column support for a preparative chromatography column, said column support comprising:
   an upper ring and a lower ring aligned along a common axis and joined to each other by peripheral spacing means to define a column space to receive a chromatography column between said rings;
   a plate detachably joinable to said upper ring in parallel relation therewith to define a gap between said plate and said upper ring;
   a rod movably joined to said plate along said axis, said rod passing through said plate and terminating in a plunger that extends into said column space when said plate and said upper ring are joined;
   drive means for moving said rod along said axis and thereby moving said plunger within said column space and between said column space and said gap when said plate and said upper ring are joined; and
   means for suspending said plate from a frame to allow a first upper and lower ring combination sized for a chromatography column of a first diameter that is joined to said plate through said upper ring to be detached from said plate, removed and replaced by a second upper and lower ring combination sized for a chromatography column of a second diameter different from the first, without changing said plate.

2. The column support of claim 1 wherein said rod is hollow and has a threaded exterior surface, and said drive means comprises a motor and gear box affixed to said plate to form a worm gear with said rod.

3. The column support of claim 1 wherein said peripheral spacing means comprises a series of parallel posts joining, and distributed around the peripheries of, said upper and lower rings.

4. The column support of claim 3 wherein said upper ring of said first ring combination, defined as a first upper ring, and said upper ring of said second ring combination, defined as a second upper ring, have equal outer diameters but differently positioned mounting sites for said posts such that posts joined to said second upper ring are closer to said axis than posts joined to said first upper ring.

5. The column support of claim 1 wherein said plunger comprises an inflatable peripheral gasket.

6. The column support of claim 5 wherein said inflatable peripheral gasket is inflated by a pneumatic supply mounted on said frame.

7. The column support of claim 1 wherein said drive means defines a path of travel of said rod along said axis and said column support further comprises means for limiting said path of travel.

\* \* \* \* \*